United States Patent [19]

Carlock

[11] 4,189,448
[45] Feb. 19, 1980

[54] POLYPYRIDINERHODIUMCARBONYL AND IRIDIUM CARBONYL HYDRIDE AND HALIDE HYDROFORMYLATION CATALYSTS

[75] Inventor: John T. Carlock, Ponca City, Okla.

[73] Assignee: Conoco, Inc., Ponca City, Okla.

[21] Appl. No.: 924,600

[22] Filed: Jul. 14, 1978

[51] Int. Cl.² ............................................. C07C 45/08
[52] U.S. Cl. ............................................. 260/604 HF
[58] Field of Search ................. 260/604 HF; 568/909

[56] References Cited

U.S. PATENT DOCUMENTS

| | | | |
|---|---|---|---|
| 3,450,730 | 6/1969 | Scheben et al. | 260/604 HF |
| 3,594,425 | 2/1971 | Brader et al. | 260/604 HF |
| 3,632,676 | 3/1972 | Kahle et al. | 260/604 HF |
| 3,636,159 | 1/1972 | Solomon | 260/604 HF |
| 3,931,332 | 1/1976 | Wilkes | 260/604 HF |
| 4,066,705 | 1/1978 | Hughes | 260/604 HF |
| 4,072,720 | 2/1978 | Haag | 260/604 HF |
| 4,098,727 | 7/1978 | Haag et al. | 260/604 HF |

Primary Examiner—Werren B. Lone

Attorney, Agent, or Firm—Cortlan R. Schupbach, Jr.

[57] ABSTRACT

Catalysts of the general structure

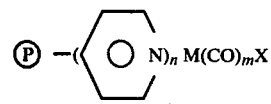

have been found to be effective heterogeneous hydroformylation catalysts at temperature of from about 60° C. to about 150° C. and hydrogen to carbon monoxide ($H_2$/CO) gas pressures of from about 100 to about 3500 psig for both primary and internal olefins. The process produces an increased amount of linear normal aldehydes. At the completion of the hydroformylation reaction, the reactor gas can be altered to essentially pure hydrogen and the catalyst then further converts aldehyde formed by the hydroformylation reaction to alcohols under the same reaction conditions. The copolymer support acts as a ligand and allows the catalyst to be easily recovered.

6 Claims, No Drawings

POLYPYRIDINERHODIUMCARBONYL AND IRIDIUM CARBONYL HYDRIDE AND HALIDE HYDROFORMYLATION CATALYSTS

This invention relates to the oxidation of olefins to aldehydes. More particularly, this invention relates to the use of a polyvinylpyridinerhodiumcarbonyl or iridium carbonyl hydride and halide-containing catalyst as a hydroformylation catalyst, the catalyst is also useful for the one reactor synthesis of alcohols.

The hydroformylation of terminal (or alpha) olefins by certain homogeneous rhodium catalysts is known in the art. Representative examples of references describing rhodium catalysts used in hydroformylation reactions and reaction conditions necessary are found in U.S. Pat. Nos. 3,917,661; 3,907,847; 3,821,311; 3,499,932; 2,527,809; 3,825,601; 3,948,999; and 3,984,478. Literature references of polymerbound catalysts include Tetrahedron Letters, 1971 (50) 4787-90, Grubbs et al, Journal of Macrmol. Sci. Chem., 1972, 13 (12), 82832. While these references are not exhaustive of the art, they appear to be representative of hydroformylation in the current state of the art. However, these catalysts and reactions are generally very poor when used with internal olefins. When these catalysts are dissolved in the reaction mixture, the catalysts are difficult to recover. Recovery of the catalyst is important since rhodium is an extremely expensive metal and the product cost rises sharply with each percentage drop in rhodium recovery from a previous reaction. In addition, these catalysts usually employ Group V ligands such as phosphines, phosphites, organo-arisines, and organoantimony compounds which are very toxic and render the catalysts air sensitive.

Hydroformylation is a reaction which converts olefins (equivalent to alkenes for the purposes of this specification and claims) to aldehydes such as shown in the formula below:

$$RC=CR \rightarrow R-CH-CR-CHO,$$

wherein R is hydrogen or an organic group. Usually the hydroformylation procedure is followed by the hydrogenation of aldehydes to produce alcohol. However, the hydrogenation procedure is relatively simple and can be carried out by any one of several well-known means. In this procedure of converting olefins to alcohols the most difficult and least efficient step is the initial hydroformylation conversion of olefins to aldehydes. In the art cited above, such conversions have been accomplished but only using catalysts which are difficult to recover and in some cases are extremely toxic.

U.S. Pat. Nos. 3,636,159 and 3,652,676 describe polymer bound hydroformylation catalysts. However, these references deal with a variety of catalysts including those which contain toxic group v ligands and which reactions are carried out in a mixture of methanol and water. It would be of great benefit to provide a catalyst system which is recoverable, contains no toxic ligands, and which allows the one reaction synthesis of olefins to alcohols in a practical manner. Conversions of internal olefins to commercially desirable primary alcohols would also be of great benefit.

It is therefore an object of the present invention to produce aldehydes containing a significant percentage of linear normal isomer from all classes of olefins, both primary and internal. It is a further object of the instant invention to provide a method for producing saturated organic compounds from unsaturated organic compounds and to produce alcohols from olefins in a single reactor. Other objects will become apparent to those skilled in this art as the description proceeds.

It has now been discovered in accordance with the present invention that a new and improved process for converting olefins to aldehydes is possible in the presence of a catalyst having the general structure

wherein said conversion is carried out at temperatures of from about 60° to about 150° C. and pressures of from about 100 to about 3500 pounds per square inch gauge (psig) in the presence of hydrogen and carbon monoxide, wherein n is from 1 to about 3, m is from 1 to about 2, M is rhodium or iridium, and X is selected from the group consisting of chlorine, bromine, iodine and hydrogen, and ⓟ is a heterocyclic nitrogen-containing polymer capable of complexing with rhodium and iridium catalyst.

The present catalysts are a distinct advantage over catalysts previously known for hydroformylation activity, such prior art catalysts being very toxic in many regards. Among such toxic prior art catalysts are esters of various trivalent phosphorus-containing acids, organo phosphorus, organoarsenic, and organoantimony compounds. These ligands are also normally found with hydroformylation catalysts, such ligands being absent in the catalyst of the instant invention.

The present catalyst is active in isomerizing the double bonds of internal olefins to an alpha position, the subsequent hydroformylation of which, yields a significant percentage of linear normal aldehydes which are easily hydrogenated to linear normal alcohols.

It has also been discovered that the catalyst of the instant invention is very active as a hydrogenation catalyst for many classes of unsaturated organic compounds. This catalyst can be used to hydrogenate hydroformylation (oxo) aldehydes to their alcohol analogues. This allows a simple, two-step, one-reactor catalyst synthesis of alcohols from olefins. This reaction is carried out by simply changing the reactor gas to essentially pure hydrogen after the oxo of hydroformylation step has been completed, then purging the system free of carbon monoxide and carrying out the reaction under hydrogenation conditions. The conditions for the hydroformylation previously carried out will suffice for hydrogenation of the aldehydes produced. The polymer bound catalyst is also useful for continuous hydroformylation reaction, utilizing the catalyst in a fixed bed reactor.

The instant invention thus preferably provides a polyvinyl pyridine/divinylbenzene copolymer as a combination support and liquid for a rhodium and/or iridium complex to form the catalyst of the instant invention. The synthesis sequence of the instant invention consists of simply dissolving the metal complex in a suitable organic solvent, placing the solution under an inert atmosphere with a heterocylic nitrogen-containing polymer for a period of time sufficient to effect reaction, and purifying the catalyst by extraction. Such a process produces the halide version of the instant catalyst.

Representative examples of heterocylic nitrogen-containing polymers useful in the instant invention are polyvinylpuridine/divinylbenzene copolymers such as 4-vinylpyridine/divinylbenzene, 3-vinylpyridine/divinylbenzene, 2-vinylpyridine/divinylbenzene; also polyphenylquinoxaline/divinylbenzene copolymer, poly[(N-vinylcarbazole)/divinylbenzene copolymer and polyvinylimidazole/divinylbenzene copolymer.

The same procedure is carried out for the hydride version of the catalyst except that after stirring in the polymer, the resulting solution is reduced with borohydride before purifying the catalyst by extraction.

The catalysts of the instant invention are recoverable and reuseable by simple means such as filtration. Filtration is carried out under an inert atmosphere. The catalysts, in addition to acting as oxo or hydroformylation catalysts can be used to hydrogenate aldehydes and other types of unsaturated organic compounds such as alkenes, alkynes, and aromatic rings to their saturated analogues.

In the general structure for the catalyst shown, n is a pyridine linkage into the polyvinyl pyridine/divinylbenzene copolymer and n can range from about 1 to about 3. However, normally, n will be from about 2 to about 3.

The number of carbonyl groups in the catalyst will depend in large part upon the pressure in the reactor during the hydroformylation of the olefins. Normally, m will range from 1 to 3 and will usually be 1 or 2. The total number of groups coordinately bonded to M is no greater than 6 or less than 4.

When the metal complex is bound to a highly crosslinked polymer (above about 20–25% crosslinking) a swelling solvent is not required for maximum efficiency. However, when the metal complex is bound to a swellable resin of low crosslinking content, a swelling solvent such as tetrahydrofuran, benzene, toluene, zylene, acetophenone and dimethylformamide can be used to increase reaction rate. Any solvent which causes the resin to swell without adversely affecting the overall catalyst can be employed. The catalysts of the instant invention are suitable for continuous fixed-bed operations.

The catalyst is more concretely described with reference to the examples below wherein all parts and percentages are by weight unless otherwise specified. The examples are provided to exemplify the instant invention and do not limit it.

In Examples 1–8 the preparation and hydroformylation activity of a polypyrididerhodiumcarbonyl hydride catalyst is illustrated. Use of the catalyst both in the hydroformylation reaction and in the hydrogenation of the aldehyde formed are shown in the examples. All olefins used in the hydroformylation reactions were percolated through a 30 centimeter × 2 centimeter silica gel column prior to use. All synthetic operations were performed under an inert gas atmosphere using flame dried glassware.

Chemical analysis refers to results obtained from gas liquid chromathograph (GLC) and infrared (IR) techniques. Metal elution was determined using X-ray fluorescence,

EXAMPLE 1

A 1% divinylbenzene 4-vinylpyridine copolymer (14 grams) was added with stirring to 50 ml of anhydrous tetrahydrofuran (THF) followed by 1.5 grams of [Rh(CO)$_2$Cl]$_2$. The mixture immediately turned a bright yellow-orange. The mixture was allowed to continue stirring for 4 hours. The treated polymer was then filtered and extracted for 10 hours with THF after which the mixture was dried in vacuum at 25° C. for 24 hours. Chemical analysis of the polymeric catalyst thus formed revealed a composition of 69.79% carbon, 6.82% hydrogen, 9.79% nitrogen, 6.97% oxygen 4% rhodium, and 1.7% chlorine.

One gram of sodium borohydride was added to 50 ml of warm absolute ethanol. The mixture was stirred and filtered. Five grams of the treated polymer as described above were added to the borohydride-ethanolic solution, followed by 20 ml of anhydrous THF. The mixture was stirred for 2 hours during which time the color of the polymer turned from bright orange-yellow to black. The polymer was filtered, extracted the THF for 70 hours, and dried at 25° C. in vacuum for three hours. Chemical analysis performed on this product indicated a composition of 61.73% carbon, 6.46% hydrogen, 9.05% nitgoren, 7.94% oxygen, 4% rhodium, and 1.4% chlorine. Infrared analysis of the product indicated that chlorine present in the polymer was present as a HCL-pyridine quaternary salt.

EXAMPLE 2

This example illustrates a general method for use of this catalyst in autoclave reactions. One gram of the catalyst described in Example 1 was stirred with 10 ml of benzene (swelling solvent) and charged into an autoclave fitted with a magnetic stirring bar. Thirty-five grams of 7-tetradecene was added. The autoclave was sealed and the system freed of argon by purging with a 1:1 mixture of hydrogen carbon monoxide four times to 900 psig. and then vented. The reactor was then heated quickly to 120° C. and the hydrogen carbon monoxide gas pressure was adjusted to 830 psig at this maximum temperature. After 23.8 hours of reaction time chemical analysis of the reaction mixture indicated a 30% conversion of 7-tetradecene to C$_{15}$ aldehydes. Further analysis of the aldehyde product indicated 13.9% of the product to be n-pentadecanal.

EXAMPLE 3

The catalyst was recovered from Example 2 by filtration and recharged into the autoclave as shown in Example 2. The reaction was run identically with that of Example 2 except that the reaction temperature was maintained at 130° C., the olefin charge consisted of 25 grams of 1-hexene, and the hydrogen carbon monoxide gas pressure was 750 psig after adjustment at maximum temperature. After 10.6 hours of reaction time, the chemical analysis of the reaction mixture indicated an 82% conversion of 1-hexene to C$_7$ aldehyde, illustrating the ease of reaction primary olefins as compared to internal olefins. Further analysis of the aldehyde product indicated in n-heptanal/branch C$_7$ aldehyde (normal/branched) ratio of 0.692.

EXAMPLE 4

The catalyst was recovered as described in Example 3. The autoclave was charged and the reaction conducted identically as illustrated in Example 3 except that the olefin charged consisted of 35 grams of 1-octane and the reaction gas pressure of hydrogen to carbon monoxide at a 1:1 mole ratio was maintained at 950 psig. After 9.6 hours of reaction time, chemical analysis of the reaction mixture indicated a 73% conversion of 1-octene to C$_9$ aldehydes. Further analysis of the aldehyde product indicated an n-nonal/branched C$_9$ aldehyde ratio of 0.577.

EXAMPLE 5

The catalyst from Example 4 was again recovered, the autoclave charged and the reaction conducted indentically with that shown in Example 3 except that the olefin charged consisted of 35 grams of 1-undecene. After 21½ hours of reaction time, chemical analysis of the reaction mixture indicated a 90% conversion of 1-undecene to $C_{12}$ aldehydes. Further analysis of the aldehyde product indicated that the normal/branched aldehyde ratio was 0.388.

EXAMPLE 6

At the conclusion of the hydroformylation reaction described in Example 5, temperature of 130° C. together with stirring was maintained while the reactor gas was purged with pure hydrogen, the system freed of carbon monoxide by purging with hydrogen 18 times to 950 psig. The hydrogen gas pressure was maintained at 950 psig. After 10 hours of reaction time, chemical analysis of the reaction mixture indicated a 100% conversion of $C_{12}$ aldehydes to $C_{12}$ alcohols and the remaining $C_{12}$ olefin was converted to n-dodecane.

EXAMPLE 7

The catalyst was recovered from the reaction carried out in Example 6 by filtration and a reaction was run identically with the conditions established in Example 3 except that the only olefinic material charged into the autoclave was 35 grams of benzene. The reaction temperature was maintained at 120° C. and hydrogen was used as the only reactor gas throughout the entire experiment. After 24 hours of reaction time, chemical analysis of the reaction mixture indicated a 27% conversion of benzene to cyclohexane.

EXAMPLE 8

The catalyst used in Example 7 was recovered by filtration, the autoclave charged and the reaction conducted identifcally as illustrated in Example 7 except that 10 ml of benzene (swelling solvent) was added, 35 grams of 1-octene employed as the olefin charge, and hydrogen gas pressure maintained throughout the reaction at 800 psig. After 1.5 hours of reaction time, chemical analysis of the reaction mixture indicated a 75% conversion of 1-octene to n-octane.

EXAMPLE 9

In order to quantify metal elution from the polymeric catalyst, the products from all above examples were sampled and analyzed for rhodium content. The results are presented in tabular form in Table 1.

The following examples illustrate the use of polypyridine rhodium carbonyl halide materials.

EXAMPLE 10

Fourteen grams of a divinylbenzene 4-vinylpyridine copolymer were added to 50 ml of anhydrous THF with stirring followed by 1.5 grams of [rhodium $(CO)_2Cl]_2$. The mixture immediately turned to bright yellow orange and was continuously stirred for four hours. The treated polymer was then filtered and extracted for 10 hours with THF after which it was dried after vacuum for 25° C. for 24 hours. Chemical analysis of the polymer catalyst revealed a composition of 69.79% carbon, 6.82% hydrogen, 9.79% nitrogen, 6.97% oxygen, 4% rhodium, and 1.7% chlorine.

EXAMPLE 11

This example sets a general method for the use of the catalyst prepared in Example 10 in autoclave reactions. One gram of the catalyst prepared in Example 10 in 10 ml of benzene (swelling solvent) was charged into an autoclave fitted with a magnetic stirring bar, followed by 35 grams of 7-tetradecene. The autoclave was sealed, purged with a 1:1 mixture of hydrogen and carbon monoxide 4 times at 900 psig. The reactor was then heated quickly in about 5 to 10 minutes to 110° C. at which temperature the 1:1 hydrogen carbon monoxide reactor gas pressure was adjusted to 950 psig. After 11.33 hours of reaction time, chemical analysis of the reaction mixture indicated a 58% conversion of 7-tetradecene to $C_{15}$ aldehydes. Further analysis of the $C_{15}$ aldehyde product revealed 11.2% of the product to be n-pentadecanal formed from catalyst promoted isomerization of the double bond to an alpha position and the subsequent hydroformylation of the primary olefin species.

EXAMPLE 12

The reaction was carried out under identical conditions with Example 11 except that the olefin charge was 35 grams of Shell 1314 (trademark of and sold by Shell Chemical Company) internal olefin mixture. The reaction temperature was maintained at 120° C. The catalyst used was recovered from Example 11 by filtration. After 12 hours of reaction time, chemical analysis of the reaction mixture indicated a 36% conversion of $C_{13}$ and $C_{14}$ olefins to $C_{14}$ and $C_{15}$ aldehydes. Further analysis of the aldehyde product showed 16.7% to be linear normal aldehydes.

EXAMPLE 13

The catalyst was recovered from the Example 12 reaction by filtration. The instant reaction was carried Table 1

| Example No. | Reactant | Product | Reactor Gas | % Conversion/ Reaction Time (Hr) | Reactor Gas Psig)/°C. | Rh Content (PPM) |
|---|---|---|---|---|---|---|
| 2 | 7-tetradecene | $C_{15}$ aldehydes | (1:1) $H_2/CO$ | 38/23.80 | 830/120 | <0.2 |
| 3 | 1-Hexane | $C_7$ aldehydes | (1:1) $H_2/CO$ | 82/10.61 | 750/130 | 0.5 |
| 4 | 1-Octene | $C_9$ aldehydes | (1:1) $H_2/CO$ | 73/9.60 | 950/130 | 0.5 |
| 5 | 1-Undecene | $C_{12}$ aldehydes | (1:1) $H_2/CO$ | 90.21.50 | 950/130 | — |
| 6 | Example 5 Product | $C_{12}$ alcohols & n-dodecane | $H_2$ | 100/10.00 | 950/130 | 0.5 |
| 7 | Benzene | Cyclohexane | $H_2$ | 27/24.00 | 950/120 | <0.7 |
| 8 | 1-Octene | n-octane | $H_2$ | 75/1.50 | 800/120 | <0.2 |
| 9 | 1,7-octadiene | n-octane | $H_2$ | 61/3.66 | 950/120 | 0.25 | out identically with Example 11 except that the olefin charge consisted of 35 grams of 1-undecene and the reaction temperature was maintained at 130° C. After 18.70 hours of reaction time, chemical analysis of the each example is presented in Table II. Rhodium elution decreased from sample to sample, but total polymeric catalyst recovery was essentially complete, subject to normal handling loss.

Table 2

| Example No. | Reactant | Product | Reaction Results | | Reactor Gas (Psig)/°C. | Rh Content (PPM) |
|---|---|---|---|---|---|---|
| | | | Reactor Gas | % Conversion/ Reaction Time (Hr) | | |
| 11 | 7-tetradecene | $C_{15}$ aldehydes | $H_2/CO$ (1:1) | 58/11.333 | 900/110 | <0.2 |
| 12 | Shell 1314 internal olefin | $C_{14}, C_{15}-$ aldehydes | $H_2/CO$ (1:1) | 36/12.0 | 950/120 | <0.17 |
| 13 | 1-undecene | $C_{12}$ aldehydes | $H_2/CO$ (1:1) | 20/18.70 | 950/130 | — |
| 14 | Example 4 product | $C_{11}$ alkane + $C_{12}$ alcohols | $H_2$ | 100/3.0 | 950/130 | 1.3 |
| 15 | 1,7-ocadiene | n-octane | $H_2$ | 84/13.66 | 900/130 | <0.2 |
| 16 | Ethyl acrylate | Ethyl propionate | $H_2$ | 100/0.38 | 900/130 | <0.2 |
| 17 | 1-undecene | n-undecane | $H_2$ | 80/5.66 | 900/130 | <0.2 | reaction mixture indicated a 20% conversion of $C_{11}$ olefins to $C_{12}$ aldehydes having a normal to isomerized ratio of 1.68.

EXAMPLE 14

The reactor and reaction mixture from Example 13 was maintained at 130° C. and was purged 15 times at 950 psig with pure hydrogen. The reactor was maintained at 950 psig of hydrogen for 3 hours at the end of which time all observed $C_{12}$ aldehydes were converted to $C_{12}$ alcohols and all remaining $C_{11}$ olefins were converted to $C_{11}$ alkane.

EXAMPLE 15

The catalyst was recovered from the Example 14 by filtration. A reaction was carried out identically with that established in Example 11 except that pure hydrogen was used as the reactor gas and the olefin charge consisted of 35 grams of 1,7-octadiene. The hydrogen reactor gas pressure was maintained at 900 psig and the reactor temperature at 130° C. After 13.66 hours of reaction time, chemical analysis of the reaction mixture indicated an 84% conversion of 1,7-octadiene to n-octane.

EXAMPLE 16

The catalyst was recovered from Example 15 reaction by filtration. The instant reaction was carried out identically with that of Example 14 except that the olefin charge consisted of 35 grams of ethyl acrylate. After 0.38 hours of reaction time, chemical analysis of the reaction mixture indicated a 100% conversion of ethyl acrylate to ethyl propionate.

EXAMPLE 17

The catalyst was recovered from the Example 16 reaction by filtration. The instant reaction was carried out identically with Example 14 except that the olefin charge consisted of 35 grams of 1-undecene. After 5.66 hours of reaction time, chemical analysis of the reaction mixture indicated an 80% conversion of 1-undecene to n-undecane.

EXAMPLE 18

The metal elution from the polymeric catalyst in the preceding examples was quantified. The products from each example were sampled and analyzed for rhodium content. The elution data together with a summary of

EXAMPLE 19

An iridium-containing catalyst is prepared by adding 50 ml of anhydrous THF to 14 grams of 1% divinylbenzene-4-vinylpyridine copolymer with stirring, followed by 1.5 grams of $[Ir(CO)_3Cl]$. Stirring is continued for 4 hours, after which the treated polymer is extracted for 10 hours with THF and dried in vacuum for 24 hours at 25° C.

One gram of sodium borohydride was added to 50 ml of warm absolute ethanol. The mixture was stirred and filtered. Five grams of the treated polymer as described above were added to the borohydride-ethanolic solution, followed by 20 ml of anhydrous THF. The polymer was filtered, extracted the THF for 70 hours, and dried at 25° C. in vacuum for three hours.

Hydroformylation reactions of the instant invention are carried out in the presence of mixtures of hydrogen and carbon monoxide. The reaction requires 1 mole of CO for each mole of olefin reacted. Normally, the ratio of hydrogen to carbon monoxide will range from about 100:1 to about 1:100, but from about 80:20 to about 20:80 is preferred, although from about 60:40 to about 50:50 respectively is preferred and 50:50 respectively is most preferred.

The instant invention thus provides a method for converting olefins to aldehydes and, if desired, further to alcohols while using a polymer bound rhodium containing catalyst which has no toxic group V ligands and is recoverable and reuseable in succeeding reactions. In addition, the instant catalysts are capable of efficient conversion of internal and primary olefins to aldehydes. Further, the instant catalysts are capable of hydrogenating a wide range of unsaturated organic compounds. The instant catalysts are highly desirable from a commercial viewpoint since low catalyst levels are possible while maintaining commercially feasible conversion rates while recovering the catalyst for reuse.

While certain embodiments and details have been shown for the purpose of illustrating this invention, it will be apparent to those skilled in this art that various changes and modifications may be made herein without departing from the spirit or the scope of the invention.

I claim:

1. A method for isomerizing internal olefins to primary olefins then hydroformylating the primary olefins formed to aldehydes in the presence of a catalyst having the general structure

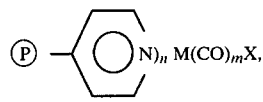

said isomerization and subsequent hydroformylation both carried out at temperatures of from about 60° C. to about 150° C. and pressures of from about 100 to about 3500 psig in the presence of carbon monoxide and hydrogen, wherein n is from 1 to about 3, m is from 1 to about 2, M is rhodium or iridium, X is selected from the group consisting of chlorine, bromine, iodine, and hydrogen, and (P) is a heterocyclic nitrogen-containing polymer selected from the group consisting of polyvinylpyridine/divinylbenzene copolymers such as 4-vinylpyridine/divinylbenzene, 3-vinylpyridine/divinylbenzene, 2-vinylpyridine/divinylbenzene; also polyphenylquinoxaline/divinylbenzene copolymer, poly[N-vinylcarbazole]/divinylbenzene copolymer and polyvinylimidazole/divinylbenzene copolymer.

2. A method as described in claim 1 wherein M is rhodium.

3. A method as described in claim 2 wherein the ratio of carbon to hydrogen is from about 80:20 to about 20:80 respectively.

4. A method as described in claim 3 wherein m is 2, and X is selected from the group consisting of bromine, chlorine, and iodine.

5. A method as described in claim 2 wherein m is 2, and X is hydrogen.

6. A method as described in claim 1 wherein the total number of groups coordinately bonded to M is no greater than 6 or less than 4.

* * * * *